(12) United States Patent
Kismarton et al.

(10) Patent No.: US 10,585,025 B2
(45) Date of Patent: Mar. 10, 2020

(54) SYSTEM AND METHOD FOR TESTING MECHANICAL PROPERTIES

(71) Applicant: THE BOEING COMPANY, Chicago, IL (US)

(72) Inventors: Max Urban Kismarton, Renton, WA (US); Brian Scott Kasperson, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 219 days.

(21) Appl. No.: 15/806,102

(22) Filed: Nov. 7, 2017

(65) Prior Publication Data

US 2019/0137373 A1 May 9, 2019

(51) Int. Cl.
*G01N 3/18* (2006.01)
*G01N 3/06* (2006.01)

(52) U.S. Cl.
CPC ............. *G01N 3/18* (2013.01); *G01N 3/068* (2013.01)

(58) Field of Classification Search
CPC ................................. G01N 3/18; G01N 3/068
USPC ........................................................... 73/800
See application file for complete search history.

(56) References Cited

U.S. PATENT DOCUMENTS

| | | | |
|---|---|---|---|
| 9,733,172 B2* | 8/2017 | Kismarton | G01N 3/02 |
| 2014/0352451 A1* | 12/2014 | Kismarton | G01N 3/02 |
| | | | 73/826 |
| 2015/0338325 A1* | 11/2015 | Kismarton | G01N 3/02 |
| | | | 73/788 |
| 2018/0259436 A1* | 9/2018 | Al-Bin-Mousa | G01N 3/42 |
| 2019/0056307 A1* | 2/2019 | Bugg | G01L 5/0033 |

* cited by examiner

*Primary Examiner* — Jamel E Williams
(74) *Attorney, Agent, or Firm* — Moore Intellectual Property Law, PLLC

(57) ABSTRACT

A system for testing mechanical properties of a test specimen includes a first climate controlled enclosure and a mechanical tester configured to apply a load to a test specimen within the first climate controlled enclosure. The system also includes a second climate controlled enclosure proximate to a view port of the first climate controlled enclosure. The second climate controlled enclosure is configured to enclose a camera, and the camera is configured to capture image data representing the test specimen. The image data includes multiple images that enable measurement of distortion of the test specimen responsive to the load.

20 Claims, 7 Drawing Sheets

SYSTEM AND METHOD FOR TESTING MECHANICAL PROPERTIES

FIELD

The present disclosure generally relates to a system and method of testing mechanical properties.

BACKGROUND

Many types of testing are used to determine mechanical material properties of a specimen. For example, several common tests are designed to subject a test specimen to a load to determine how (or how much) the test specimen deforms under the load. As another example, several common tests are designed to subject a test specimen to a load to determine how the test specimen breaks or how much load is required to break the test specimen.

To be useful, each test should be repeated many times to determine average or characteristic properties of the material being tested. Such repeated testing can be very time consuming and expensive. For example, manually preparing each test specimen and correctly positioning each test specimen in a tester generally requires a skilled technician at least several minutes per test. Further, after each test, the technician has to remove the previous specimen and prepare the tester and the next specimen for the next test, which requires additional time.

The time and expense associated with material testing can increase significantly if special test conditions are needed to perform the test. For example, to determine high temperature material properties of a material, the material may be subjected to a load while in a temperature controlled environment. In this example, the technician may have wait for a temperature change to occur between testing each test specimen. To illustrate, if high temperature testing is to occur at a target temperature significantly above room temperature, the technician may prepare a test specimen in a room temperature environment, attach the test specimen to a tester (which generally will entail opening the temperature controlled environment), and then wait for the temperature controlled environment to stabilize at the target temperature before initiating the test. This cycle is repeated for each test. Thus, each high temperature test can require many times as long to conduct as would be needed to conduct the same test at room temperature. Similar issues arise with testing in other controlled environments, such as low temperature testing and humidity controlled testing.

SUMMARY

In a particular embodiment, a system for testing mechanical properties of a test specimen includes a first climate controlled enclosure and a mechanical tester configured to apply a load to a test specimen within the first climate controlled enclosure. The system also includes a second climate controlled enclosure proximate to a view port of the first climate controlled enclosure. The second climate controlled enclosure is configured to enclose a camera, and the camera is configured to capture image data representing the test specimen. The image data includes multiple images that enable measurement of distortion of the test specimen responsive to the load.

In another particular embodiment, a system for testing mechanical properties of a test specimen includes a camera mount coupled to an arm. The camera mount is configured to retain a camera in a position to capture image data representing a test specimen while a mechanical tester applies a load to the test specimen. The image data includes multiple images that enable measurement of distortion of the test specimen responsive to the load. The optical measurement system also includes a shock isolation system configured to couple the arm to a portion of a test system that includes the mechanical tester. The shock isolation system is configured to automatically disengage responsive to a shock due to a failure of the test specimen.

In another particular embodiment, a method of testing mechanical properties of a test specimen includes capturing, using a camera, image data representing a test specimen while a mechanical tester applies a load to the test specimen. The image data includes multiple images that enable measurement of distortion of the test specimen responsive to the load. The method also includes, while capturing the image data, directing a dry gas across the camera and at least a portion of a view port between the camera and the test specimen. The method also includes disengaging a shock isolation system coupled to the camera, where the shock isolation system disengages automatically responsive to a shock resulting from a failure of the test specimen.

The described features, functions, and advantages may be achieved independently in various embodiments or may be combined in yet other embodiments further details of which can be seen with reference to the following description and drawings.

DETAILED DESCRIPTION

Figure 1:
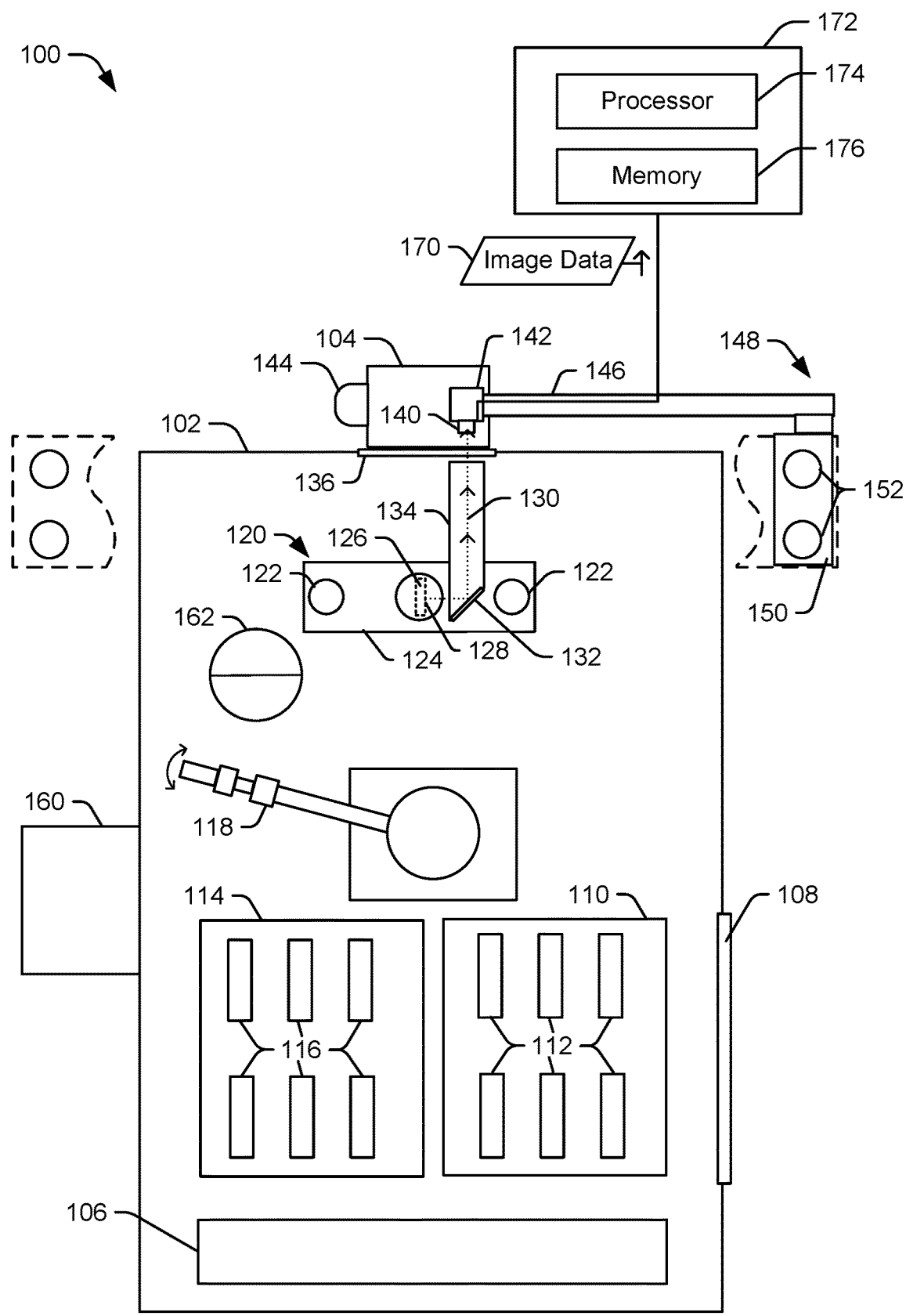
FIG. 1 is a block diagram illustrating a particular embodiment of a system for testing mechanical properties of a test specimen.

As used herein, various terminology is used for the purpose of describing particular implementations only and is not intended to be limiting of implementations. For example, the singular forms "a," "an," and "the" are intended to include the plural forms as well, unless the context clearly indicates otherwise. It may be further understood that the terms "comprise," "comprises," and "comprising" may be used interchangeably with "include," "includes," or "including." Additionally, it will be understood that the term "wherein" may be used interchangeably with "where." As used herein, "exemplary" may indicate an example, an implementation, and/or an aspect, and should not be construed as limiting or as indicating a preference or a preferred implementation. As used herein, an ordinal term (e.g., "first," " "second," "third," etc.) used to modify an element, such as a structure, a component, an operation, etc., does not by itself indicate any priority or order of the element with respect to another element, but rather merely distinguishes the element from another element having a same name (but for use of the ordinal term). As used herein, the term "set" refers to one or more of a particular element, and the term "plurality" refers to multiple (e.g., two or more) of a particular element.

Time and expense associated with testing mechanical material properties of a specimen can be decreased by automating portions of a test process. However, automating a test process raises additional issues. For example, some types of tests measure deformation of a test specimen using an extensometer or strain gauge to detect deformation of the test specimen. For some tests, multiple strain gauges are attached to a single test specimen, and each strain gauge is a rather expensive, single-use item. Further, attachment of a test specimen to an extensometer or strain gauge requires significant dexterity. Thus, automating attachment of the test specimen to the extensometer or strain gauge may entail significant capital expenditure to acquire a material handling system with sufficient dexterity.

Some tests measure deformation of a test specimen using an optical measurement system. For example, an optically detectable surface treatment (e.g., paint or ink) can be applied to a test specimen. In this example, during testing, changes in relative positions of, shape of, or dimensions of the optically detectable surface treatment can be measured to measure the deformation of the test specimen.

While using an optical measurement system avoids issues with automating attachment of extensometers or strain gauges to a test specimen, optical measurement systems can raise new issues. For example, optical measurements systems use high-quality imaging devices (e.g., cameras), that may be damaged by exposure to high-temperature, low-temperature, or high-humidity environments. Thus, it is a significant challenge to use optical measurement systems for testing material properties in extreme environments.

Embodiments disclosed herein overcome the challenges of using optical measurement systems for testing material properties in extreme environments. In particular, in the disclosed embodiments, at least a portion of a mechanical tester is disposed within a first climate controlled enclosure. The mechanical tester includes jaws or grippers to receive an article under test (e.g., a test specimen) and to apply a load to the article under test. Components of an optical measurement system (e.g., a camera and associated support hardware) are positioned external to the first climate controlled enclosure. The camera is positioned to capture images through a view port of the first climate controlled enclosure.

The first climate controlled enclosure includes a climate control system to adjust and control environmental conditions (e.g., temperature, humidity, or both) within the first climate controlled enclosure. To decrease time between tests, multiple test specimens (e.g., test coupons) can be placed in the first climate controlled enclosure at a time, and a manipulator (e.g., a robot arm) moves one test specimen at a time to the mechanical tester, and remove the test specimen after testing. Thus, two or more test specimens can be tested without opening the first climate controlled enclosure, thereby avoiding time to adjust and re-stabilize the environmental conditions within the first climate controlled enclosure between tests.

Certain environmental conditions within the first climate controlled enclosure present challenges to optical measurement through the view port. For example, during low-temperature testing, condensation can form on an external surface of the view port. Such condensation can be limited by insulating the view port, such as by forming the view port using several layers of glass separated from one another by a gas filled regions. However, using an insulated view port tends to introduce optical aberrations due to scattering effects of each layer of glass. Thus, while using multiple layers of glass can avoid condensation issues during low temperature testing, it tends to decrease image quality for all test regimes (e.g., low temperature, high temperature, and high humidity). To avoid condensation issues without decreasing image quality, particular embodiments disclosed herein house the camera and at least a portion of the view port within a second climate controlled enclosure. Within the second climate controlled enclosure, a dry gas (such as dry nitrogen) is blown across the camera and the portion of the view port. The dry gas has little or no water content; thus, the dry gas in contact with the view port does not cause condensation even when the view port includes a single layer of glass. Further, the dry gas can be heated (or cooled) to keep the camera at a prescribed operating temperature regardless of the temperature within the first climate controlled environment. For example, during high-temperature testing, convection waves may form and cause blurring of the view port (or a lens of the camera). The dry gas may be cooled and blown across the camera and the portion of the view port to reduce (or eliminate) the convection waves, thereby improving image quality.

For certain configurations, the mechanical tester may be arranged such that a surface of the test specimen to be imaged by the camera is not facing the view port. In such configurations, a mirror (or periscope) is positioned within the first climate controlled environment to direct light from the surface of the test specimen to be imaged toward the camera. The mirror can be enclosed within a housing to avoid damage or fouling by debris from the test specimen.

An additional challenge with optical measurement is keeping the camera in position relative to the test specimen during testing and between tests (e.g., from one test to the next test). In particular implementations disclosed herein, the camera is coupled to a test system that includes the mechanical tester (e.g., to a portion of a test frame). While coupling the camera to the test system maintains the camera in position relative to the test specimen, it can cause the camera to be subjected to significant shock due to failure of the test specimen. For example, when the mechanical tester performs certain tests, the test specimen may be loaded to failure. At failure of the test specimen, the test system experiences a significant shock as the test specimen releases the load all at once. Such shocks can damage to the camera if the camera is attached to the test system. Certain embodiments disclosed herein include a shock isolation system between the test system and the camera. The shock isolation system automatically disengages responsive to a high shock event (e.g., a shock with a magnitude that satisfies a release threshold) and automatically resets after the high shock event. Thus, the disclosed system enables automation of mechanical testing in a manner that significantly reduces time per test and with relatively low capital expenditure (e.g., relative to providing high dexterity robots to perform certain test steps).

FIG. 1 is a block diagram illustrating a particular embodiment of a system 100 for testing mechanical properties of a test specimen. As described further below, the system 100 uses optical measurement of distortion of the test specimen, which can simplify automation of the test process. The system 100 enables testing through a wide range of environmental conditions and includes features that facilitate use of optical measurements throughout the range of environmental conditions.

The system 100 includes a first climate controlled enclosure 102 and a mechanical tester 120 at least partially disposed within the first climate controlled enclosure 102. For example, in FIG. 1, the mechanical tester 120 includes grippers 124 that are configured to hold a test specimen 126 during a test process. In this example, the grippers 124 are disposed within the first climate controlled enclosure 102. In some implementations, another portion of the mechanical tester 120 is located external to the first climate controlled enclosure 102. For example, in FIG. 1, the grippers 124 are constrained to movement along one axis by guide rails 122. The guide rails 122 may extend through the first climate controlled enclosure 102. As another example, a load application device (e.g., an electric actuator, a pneumatic actuator, or a hydraulic actuator) can be positioned eternal to the first climate controlled enclosure 102 and mechanically linked to the grippers 124. The load application device is configured to apply a load to the test specimen 126 via the grippers 124.

In the example illustrated in FIG. 1, a manipulator 118 is disposed within the first climate controlled enclosure 102. The manipulator 118 includes one or more robot arms, a gantry system, or another electromechanical system configured to move material within the first climate controlled enclosure 102. The manipulator 118 is configured to retrieve a test specimen or test coupon (e.g., the test specimen 126) from a location within the first climate controlled enclosure 102 and to position the test specimen 126 in the mechanical tester 120. The manipulator 118 may also be configured to remove the test specimen 126 from the mechanical tester 120 after a test and to dispose of the test specimen 126 (e.g., via a disposal slot 162). In the example illustrated in FIG. 1, the location from which the manipulator 118 retrieves test specimens corresponds to a coupon holder, such as representative coupon holders 110 and 114. In this example, multiple test specimens, such as test specimens 112 and 116, can be inserted into the first climate controlled enclosure 102 via an opening 108 (e.g., a slot or door). By inserting multiple test specimens 112, 116 into the first climate controlled enclosure 102 at one time, climate variations (e.g., temperature or humidity variations) within the first climate controlled enclosure 102 can be limited, thereby reducing or eliminating delays between tests due to adjusting the climate conditions or waiting for the climate conditions to stabilize.

The system 100 also includes a climate control system 106 coupled to or within the first climate controlled enclosure 102. The climate control system 106 is configured to adjust and control the climate conditions within the first climate controller enclosure 102. For example, the climate conditions can vary depending on the specific test conditions. To illustrate, in addition to room temperature testing, the system 100 may be used for high temperature testing. High temperature testing can subject the test specimen 126 to a load while the temperature within the first climate controlled environment is greater than 100 degrees Celsius or even greater than 200 degrees Celsius. Further, in some implementations, the system 100 may be used for low temperature testing. Low temperature testing can subject the test specimen 126 to a load while the temperature within the first climate controlled environment is less than 0 degrees Celsius or even less than −70 degrees Celsius. Thus, the climate control system 106 is configured to control the temperature within the first climate controlled enclosure 102 through a range of temperatures from less than 0 degrees Celsius to greater than 100 degrees Celsius. In some implementations, the climate control system 106 is configured to control the temperature within the first climate controlled enclosure 102 through a range of temperatures from less than −70 degrees Celsius to greater than 200 degrees Celsius. In addition to, or instead of, controlling the temperature within the first climate controlled enclosure 102, the climate control system 106 may be configured to control other climate conditions, such as humidity, within the first climate controlled enclosure 102.

A control system 160 is coupled to, and configured to provide control signals to, the manipulator 118, the climate control system 106, an actuator of the disposal slot 162, an actuator of the grippers 124, a load application device of the mechanical tester 120, or a combination thereof. The control system 160 includes a processor and memory (not shown), and the memory stores instructions that are executable by the processor to transmit control signals to various components of the system 100 to implement a test. For example, an operator or technician can program the control system 160 to implement particular tests for a set of test specimens. In this example, the operator or technician may specify test operations by selecting (e.g., via a graphical user interface) from a set of preprogrammed operations. To illustrate, the operator or technician can indicate to the control system 160 a type of coupon holder used to hold a set of test specimens, and based on the type of coupon holder, the control system 160 provides machine instructions to the manipulator 118 to indicate movements to be performed by the manipulator 118 to pick up each test specimen. As another example, the operator or technician may indicate a type of test to be performed, such as a high temperature ultimate tensile strength test. In this example, the control system 160 can send data or a signal indicating a climate control setpoint (or setpoints) to the climate control system 106. When the climate control system 106 indicates that the climate control setpoint is achieved, the control system 160 can initiate a test on a test specimen, e.g., by directing a load application device to apply a load to the test specimen 126. The control system 160 may also send a signal to a camera 140 to begin capturing images of the test specimen.

In the example illustrated in FIG. 1, the camera 140 is positioned outside the first climate controlled enclosure 102. The camera 140 is configured to capture image data 170 representing the test specimen 126. In a particular implementation, the image data 170 includes multiple images that enable measurement of distortion of the test specimen 126 responsive to the load. For example, the multiple images can include an initial image captured before the load is applied or before the test specimen 126 undergoes distortion. In this example, the multiple images also include one or more additional images captured while the load is applied to the test specimen 126.

At least one surface (e.g., a surface 128) of the test specimen 126 may be treated with a surface treatment that enables a computing device 172 to measure distortion of the test specimen 126 due to the load. For example, a paint or ink may be applied randomly to the surface 128. To illustrate, paint can be sprayed in a fine mist that is allowed to settle on the surface 128 to form a discontinuous layer of paint dots on the surface 128. In this example, distortion of the test specimen 126 can be measured by measuring relative positions of two or more of the paint dots. In other examples, a paint or ink can be applied to the surface 128 according to a prescribed pattern (rather than randomly). If a material used to form the test specimen 126 inherently includes optically detectable features (e.g., fibers) on the surface 128, no surface treatment may be used.

In the example illustrated in FIG. 1, the computing device 172 includes a processor 174 and a memory 176. The memory 176 stores instructions that are executable by the processor 174 to detect features on the surface 128 of the test specimen 126 based on the image data 170 and to measure differences in position of the features in two or more image frames. For example, the measured differences in position of the features can correspond to two or more paint dots on the surface 128 moving closer together or further apart as the load is applied. Although FIG. 1 illustrates the control system 160 as a distinct component from the computing device 172, in some implementations, the control system 160 is combined with the computing device 172. In other implementations, the computing device 172 can be omitted from the system 100. In such implementations, a memory connected to or onboard the camera 140 stores the image data 170 for later processing by a computing device. Further, although FIG. 1 shows the camera 140 connected to the computing device 172 via a wired interface, in other implementations, the camera 140 may communicate with the computing device 172 via a wireless communications interface or via a network.

The camera 140 is positioned proximate a view port 136 of the first climate controlled enclosure 102. In some implementations, the view port 136 includes a single layer of glass (or another optically transparent medium) to limit optical aberrations. In such implementations, to limit or avoid condensation on an exterior surface of the view port 136, the camera 140 and at least a portion of the view port 136 are enclosed within a second climate controlled enclosure 104. In some implementations, the second climate controlled enclosure 104 includes or is coupled to a dry gas circulation system 144. In such implementations, the dry gas circulation system 144 is configured to route dry gas (e.g., dry nitrogen) across at least a portion of the camera 140 and at least a portion of the view port 136. The dry gas limits exposure of the surface of the view port 136 to ambient atmospheric gases, humidity from which would otherwise condense on the view port 136 when low temperature tests are being performed in the first climate controlled enclosure 102. The dry gas may reduce the incidence of dust and other contaminants fouling the view port 136 and a lens of the camera 140. Further, in some implementations, the dry gas circulation system 144 controls a temperature of dry gas such that the camera 140 is exposed to a relatively narrow range of temperatures as compared to the range of temperatures used for testing the first climate controlled enclosure 102. For example, the dry gas within the second climate controlled enclosure 104 may be heated when low temperature testing is being performed in the first climate controlled enclosure 102 and/or the dry gas within the second climate controlled enclosure 104 may be cooled when high temperature testing is being performed in the first climate controlled enclosure 102. Blowing the dry gas across the view port 136 or a lens of the camera 140 may reduce (or eliminate) convection waves that form during high temperature testing. For example, the high temperatures may cause convection waves (e.g., convection currents) to form, and the convection waves may reduce image (or viewing) quality at the view port 136 or a lens of the camera 140. The dry gas may "break up" (e.g., reduce or eliminate) the convection waves, thereby improving image (or viewing) quality at the view port 136 or the lens of the camera 140.

In the example illustrated in FIG. 1, the mechanical tester 120 is oriented in the first climate controlled enclosure 102 such that the surface 128 of the test specimen 126 represented in the image data 170 does not face the view port 136. A mirror 132 is disposed within the first climate controlled enclosure 102 and positioned to reflect light 130 from the surface 128 of the test specimen 126 through the view port 136 and toward the camera 140. The mirror 132 may be at least partially enclosed within a housing 134. The housing 134 protects the mirror 132 from debris generated by failure of the test specimen 126 during testing. In some implementations, the housing 134 includes padding to protect the mirror 132 from shock. Interior surfaces of the housing 134 may include an antireflective coating (e.g., a matte black paint) to reduce reflections within the housing 134.

In the example illustrated in FIG. 1, the camera 140 is coupled to a camera mount 142, and the camera mount 142 is coupled to an arm 146. The arm 146 and camera mount 142 retain the camera 140 in position to receive the light 130 reflected from the surface 128 of the test specimen 126. In some implementations, the camera mount 142 is adjustable in one or more directions to align the camera 140 to capture the image data 170.

In FIG. 1, the arm 146 is supported by a bracket 150 that is coupled to a portion of a test frame 152. A shock isolation system 148 is disposed between the bracket 150 and the arm 146. The shock isolation system 148 is configured to automatically disengage responsive to a shock having a magnitude that satisfies a release threshold. The shock isolation system 148 is also configured to automatically reset and reengage after disengaging. For example, when the mechanical tester 120 subjects the test specimen 126 to sufficient load, the test specimen 126 can fail (e.g., break), which results in rapid instantaneous release of energy in the form of mechanical shock, which propagates through portions of the system 100, including the test frame 152. The shock can be of sufficient magnitude to damage the camera 140. The shock isolation system 148 releases a mechanical interface between the arm 146 and the bracket 150 when the magnitude of the shock is sufficiently high (e.g., greater than a threshold) to limit propagation of the shock through the arm 146 to the camera 140. After the shock, the mechanical interface between the arm 146 and the bracket 150 resets to realign the camera 140 to capture images of the next test specimen.

Figure 2:
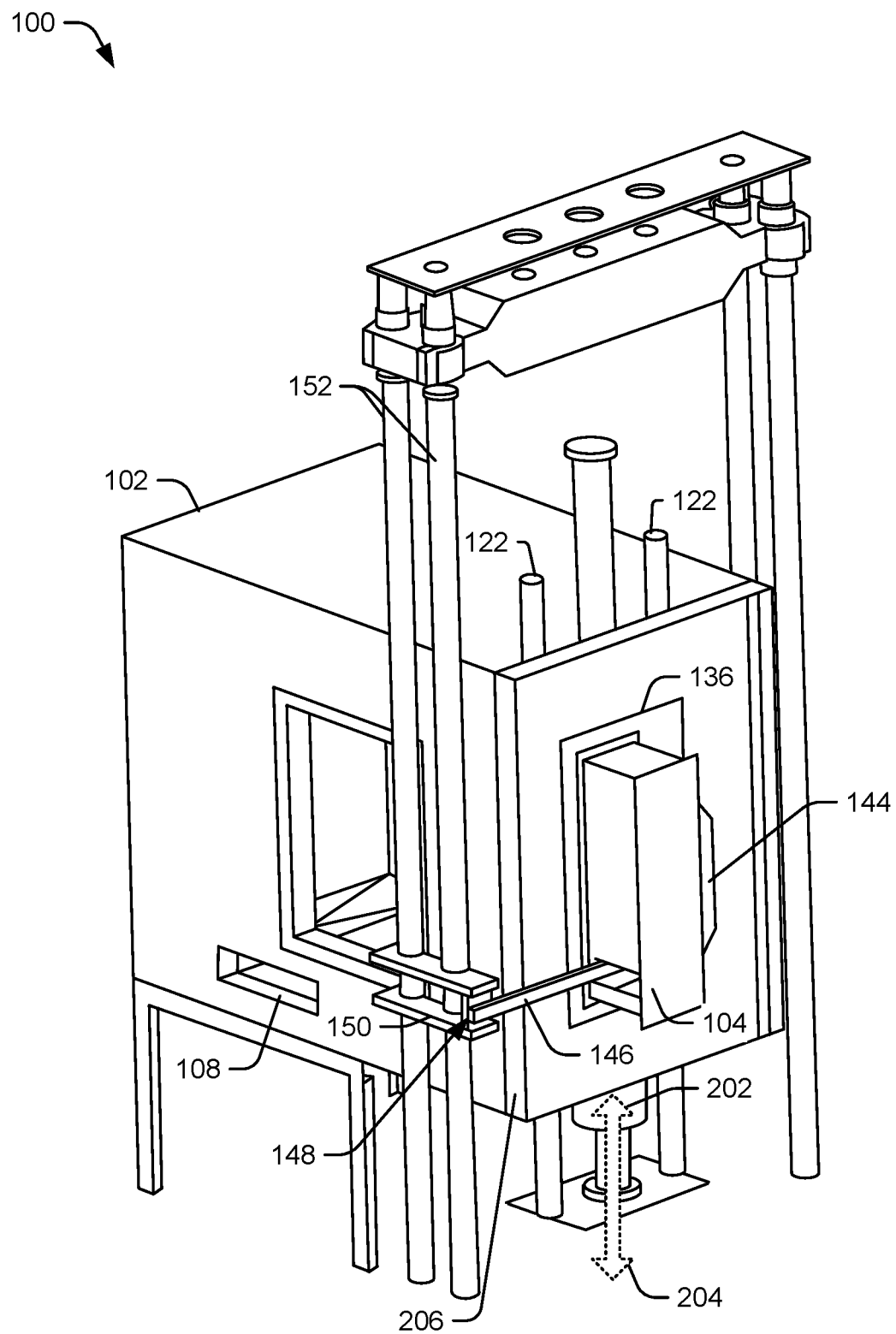
FIG. 2 is a diagram illustrating a perspective view of a particular implementation of the system of FIG. 1.

FIG. 2 is a diagram illustrating a perspective view of a particular implementation of the system 100 of FIG. 1. In the implementation illustrated in FIG. 2, portions of the test system, including the test frame 152, ends of the guide rails 122, and a load application device 202 are shown. In the illustrated implementation, the load application device 202 is configured to apply a load 204 in a first direction (e.g., a tensile load) or a second direction (e.g., a compressive load). In other implementations, the load application device 202 is configured to apply different types of loads, such as a twisting load.

FIG. 2 also shows exterior surfaces of the first climate controlled enclosure 102 and the second climate controlled enclosure 104. In FIG. 2, the first climate controlled enclosure 102 includes a slot corresponding to the opening 108 of FIG. 1. In FIG. 2, the first climate controlled enclosure 102 includes a door 206, and the view port 136 is in the door 206. In this arrangement, the shock isolation system 148 can include a hinge that allows the arm 146 to swing out of the way to enable opening the door 206. A back cover of the second climate controlled enclosure 104 may be removable to allow the arm 146 to swing on the hinge.

Figure 3:
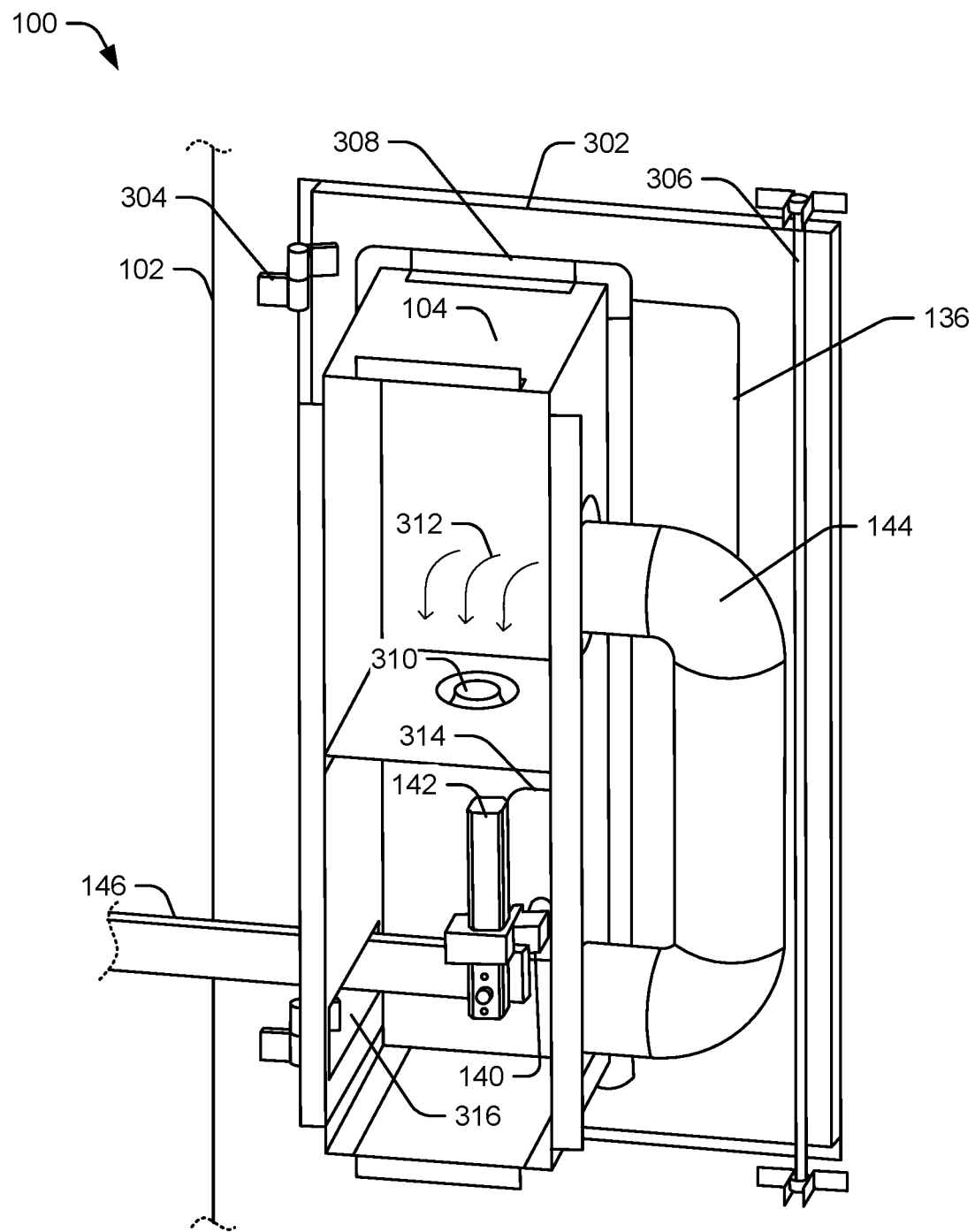
FIG. 3 is a diagram illustrating a more detailed perspective view of a portion of the system in the particular implementation illustrated in FIG. 2.

FIG. 3 is a diagram illustrating a more detailed perspective view of a portion of the system 100 in the particular implementation illustrated in FIG. 2. FIG. 3 illustrates the second climate controlled enclosure 104 with a back cover omitted or removed.

In FIG. 3, the view port 136 is within a door 302. The door 302 may be included within the door 206 of FIG. 2, or the door 302 may correspond to the door 206. The door 302 is coupled to (and moveable on) one or more hinges 304 The hinges 304 are coupled to the first climate controlled enclosure 102. Additionally, in FIG. 3, the door 302 is held closed by a latch 306.

In FIG. 3, the second climate controlled enclosure 104 is coupled via one or more flanges 308 to the door 302. The second climate controlled enclosure 104 is positioned such that at least a portion 314 of the view port 136 is within the second climate controlled enclosure 104. In some implementations, the entire view port 136 may be within the second climate controlled enclosure 104.

The arm 146 passes through an opening 316 in a side of the second climate controlled enclosure 104. The opening 316 may be filled or partially filled with a sealing material (not shown), such as foam or a flexible seal, to allow movement of the arm 146 relative to the second climate controlled enclosure 104 and to limit leakage of dry gas 312 out of the second climate controlled enclosure 104 via the opening 316.

The camera mount 142 is coupled to the arm 146, and the camera 140 is coupled to the camera mount 142. In the example illustrated in FIG. 3, a position of the camera 140 can be adjusted by moving the camera mount 142 along the arm 146 or moving the camera 140 up or down on the camera mount 142.

FIG. 3 illustrates the dry gas circulation system 144 including a fan 310 that is configured to circulate the dry gas 312 within the second climate controlled enclosure 104. In particular, the fan 310 is positioned to blow the dry gas 312 across the portion 314 of the view port 136 that is disposed within the second climate controlled enclosure 104 and across at least a portion of the camera 140 (e.g., a lens of the camera 140). In other implementations, the fan 310 can be omitted and the dry gas 312 can be provided by a pressurized source (e.g., a gas bottle).

Figure 4:
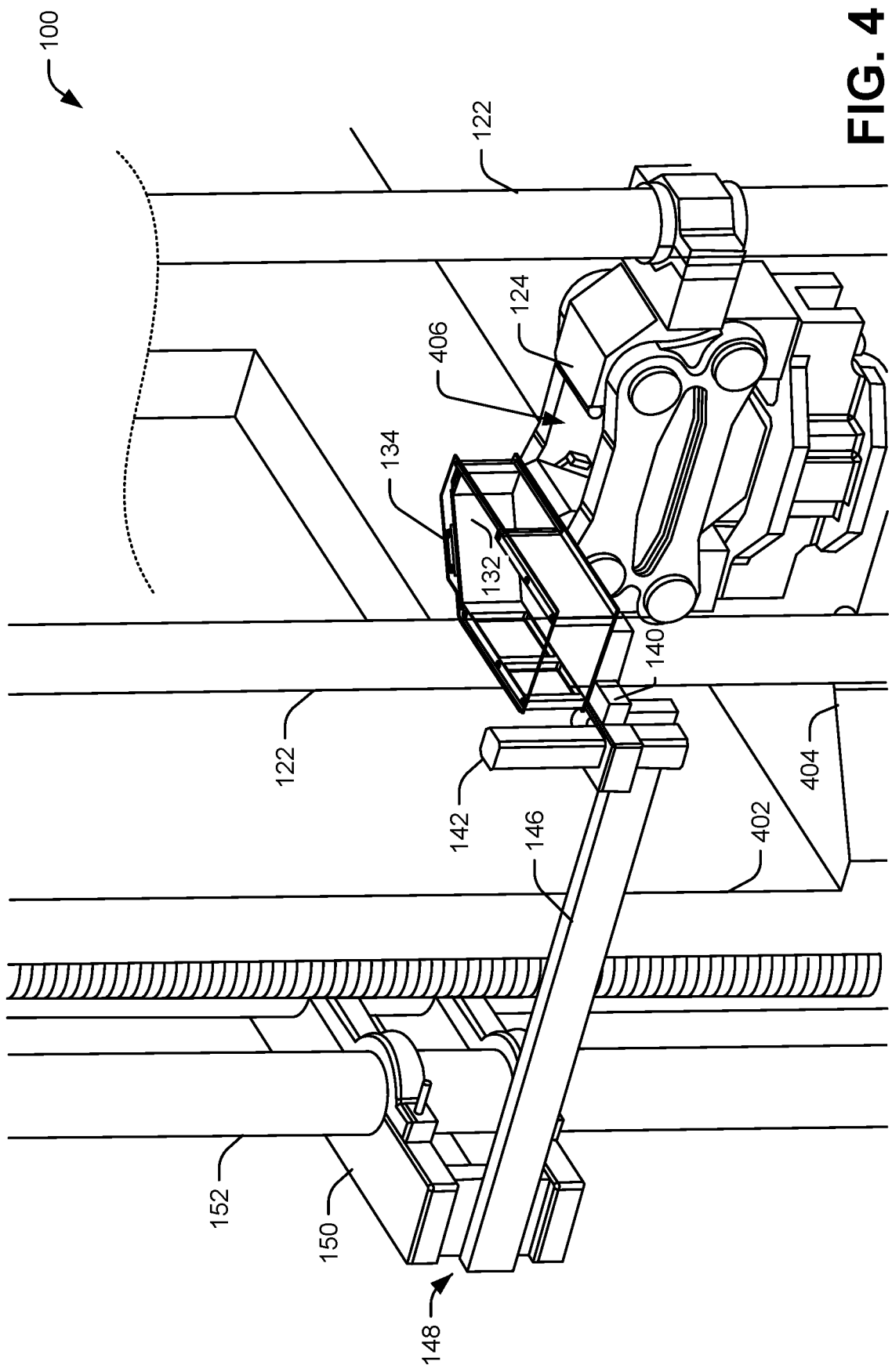
FIG. 4 is a diagram illustrating a cut away perspective view of a portion of the system in the particular implementation illustrated in FIG. 2.

FIG. 4 is a diagram illustrating a perspective view of a portion of the system 100 in the particular implementation illustrated in FIG. 2. In particular, FIG. 4 illustrates a portion of the first climate controlled enclosure 102 with the door 206 and the second climate controlled enclosure 104 omitted or removed. In FIG. 4, relative positions of the camera 140, the mirror 132, and a bottom gripper of the grippers 124 can be seen. During testing, a test specimen, such as the test specimen 126 of FIG. 1, is placed in an opening 406 of the bottom gripper and a corresponding opening of a top gripper (not shown). The grippers 124 close to grip the test specimen, and the load application device 202 of FIG. 2 applies the load 204 to the test specimen. The load 204 can be compressive (e.g., tending to move the grippers 124 toward each other) or tensile (e.g., tending to move the grippers 124 away from each other).

The mirror 132 reflects light from a surface of the test specimen toward the camera 140, and the camera 140 captures images of the surface. The images represent features of the surface that are optically detectable to enable measurement of distortion of the test specimen as a result of the load 204.

During some mechanical tests, the test specimen may be loaded until it fails (e.g., breaks). To illustrate, during an ultimate tensile strength test, the test specimen is loaded until the load 204 causes the test specimen to break. In this example, when the test specimen breaks, the grippers 124 move rapidly away from one another to some preset limit, and impart a significant shock to walls 402, 404 of the first climate controlled enclosure 102, to the guide rails 122, to the test frame 152, or to other portions of the test system. The shock isolation system 148 limits propagation of the shock from the bracket 150 to the arm 146, thereby protecting the camera 140.

Figure 5:
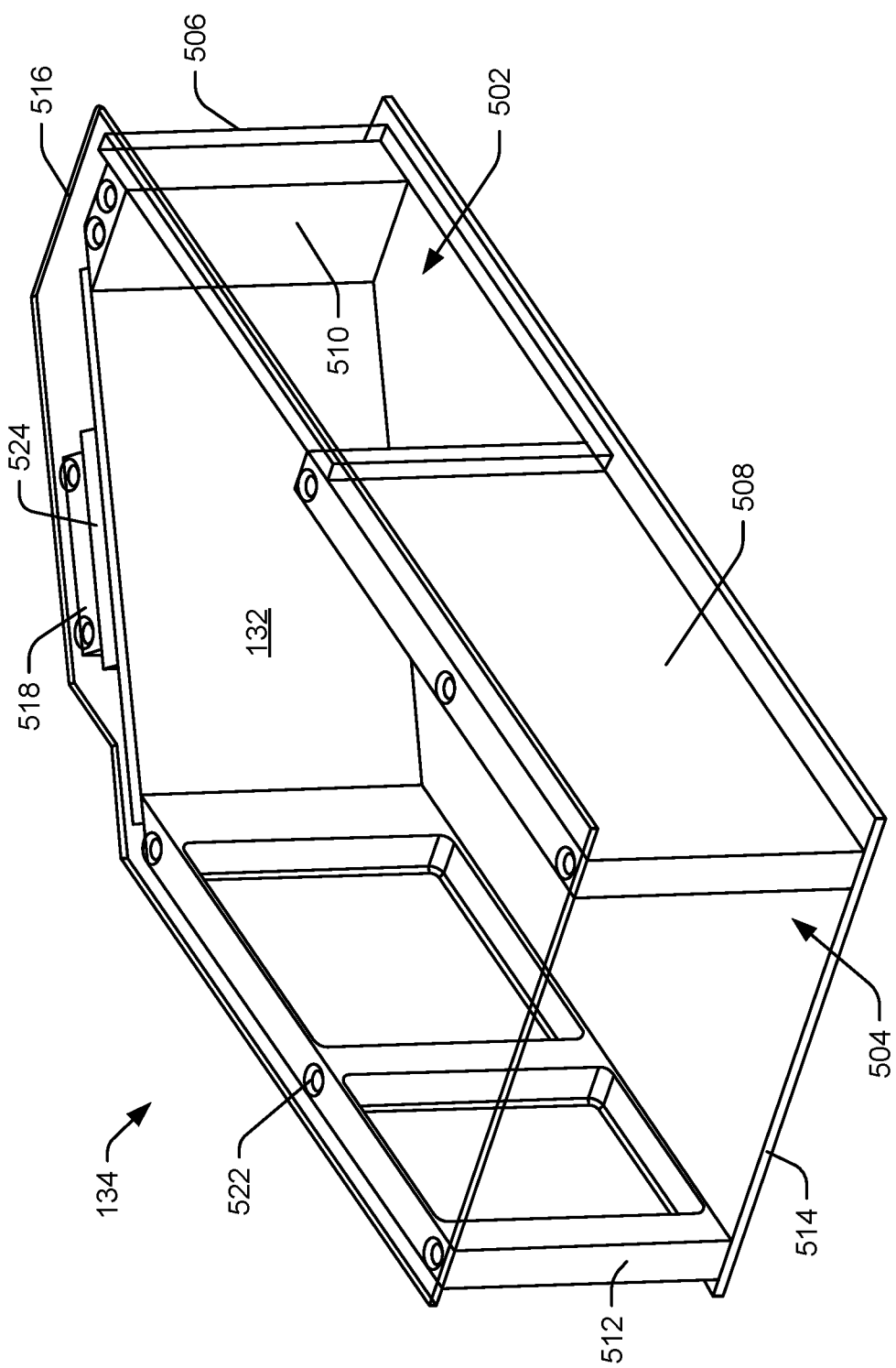
FIG. 5 is a diagram illustrating a more detailed view of a portion of the system in the particular implementation illustrated in FIG. 2.

FIG. 5 is a diagram illustrating a more detailed perspective view of a portion of the system 100 in the particular implementation illustrated in FIG. 2. In particular, FIG. 5 illustrates a particular implementation of a periscope arrangement including the housing 134 and the mirror 132. The housing 134 includes a plurality of walls, including walls 508, 510, 512, 514, 516, and 518.

Internals surfaces of at least some of the walls 508-518 may be treated to reduce glare and surface reflections from the walls 508-518. For example, the internal surfaces of the walls 508-516 may have a matte black coating. The internal surface of the wall 518 can be left untreated since it is covered by the mirror 132.

The walls 508-518 are formed of a material that is stable and durable (e.g., able to withstand shock) through the wide range of temperatures used for testing within the first climate controlled enclosure. Since the testing temperature can range from below −70 degrees Celsius to above 200 degrees Celsius, in particular implementations, the walls 508-514 are formed of metal, ceramic, or glass materials. However, in some implementations, such as when a smaller operating temperature range is needed, polymers can be used. Side walls 508-512, and 518 are joined to a top wall 516 and a bottom wall 514 via fasteners 522.

The housing 134 defines an opening 502 between the wall 508 and the wall 510 to allow light from the surface of the test specimen to pass into the housing 134 and to be reflected by the mirror 132. The housing 134 defines another opening 504 between the wall 508 and the wall 512 to allow light reflected by the mirror 132 to be directed toward the camera 140. In some implementations, an optically transparent cover 506 is positioned over the opening 502. The cover 506 protects the mirror 132 from damage or fouling by debris generated by the mechanical tester 120.

A layer of padding 524 is positioned between the wall 518 and a back surface of the mirror 132. The padding 524 protects the mirror 132 from shock resulting from tests performed by the mechanical tester 120.

Figure 6:
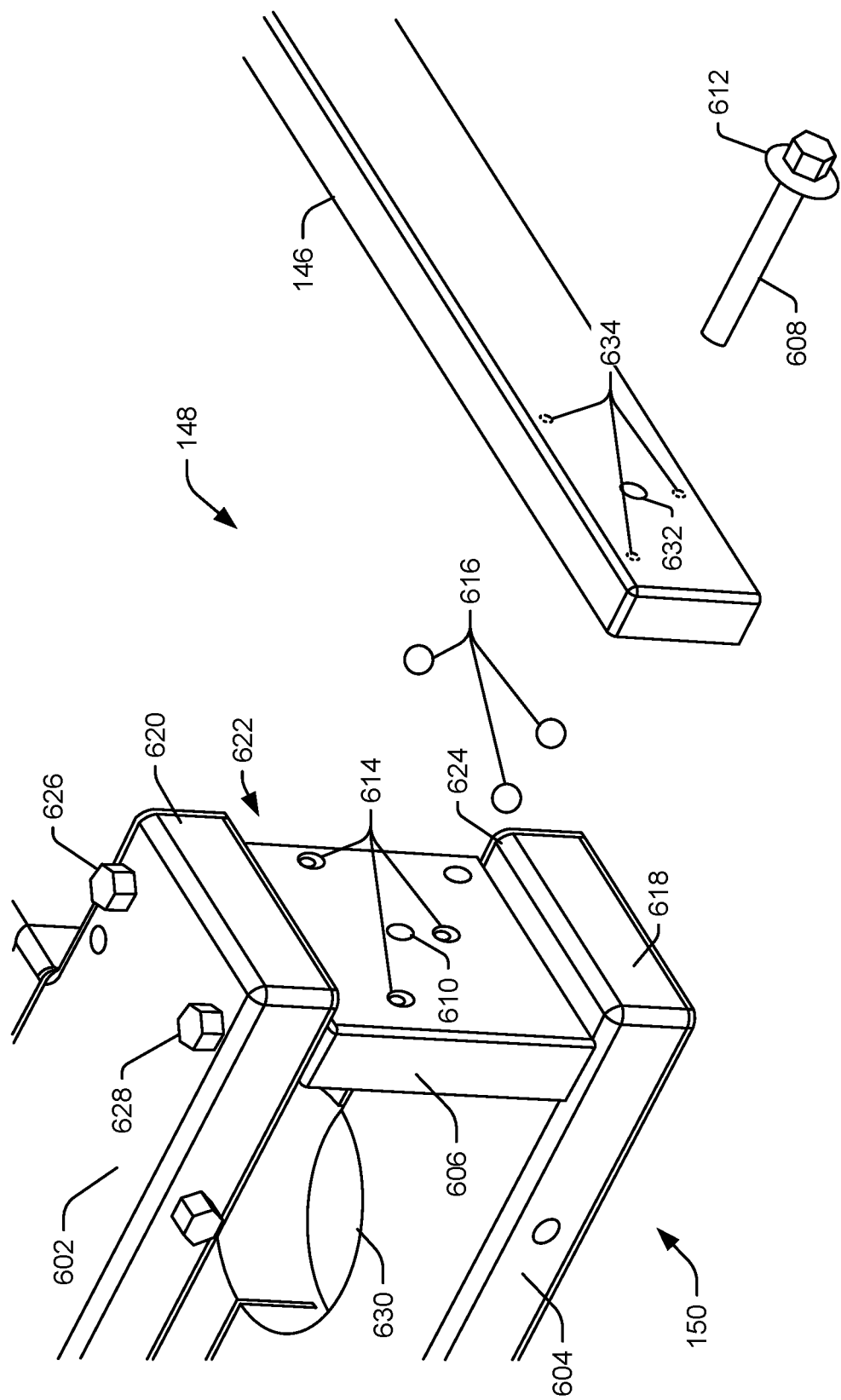
FIG. 6 is a diagram illustrating an exploded view of a portion of the system in the particular implementation illustrated in FIG. 2.

FIG. 6 is a diagram illustrating an exploded view of a portion of the system 100 in the particular implementation illustrated in FIG. 2. In particular, FIG. 6 illustrates features of the shock isolation system 148, the bracket 150, and the arm 146.

In the example illustrated in FIG. 6, the bracket 150 includes a top member 602, a bottom member 604, and a wall 606 between the top member 602 and the bottom member 604. The bottom member 604 includes an opening 630 to receive and be coupled to a portion of the test system, such as the test frame 152. The top member 602 includes a similar opening to receive and be coupled to a portion of the test system, though the opening of the top member 602 is not shown in FIG. 6. In FIG. 6, the wall 606 is inset from an end 618 of the bottom member 604 and inset from an end 620 of the top member 602 such that the top member 602, the bottom member 604, and the wall 606 define a recess 622 in which at least a portion of the arm 146 is disposed. A portion 624 of the end 618 and the end 620 may be rounded, sloped, or chamfered.

The wall 606 is coupled to the top member 602 and the bottom member 604 via a plurality of fasteners, such as a first bolt 626 and a second bolt 628. In some implementations, the second bolt 628 is configured to act as a hinge for the arm 146. For example, when the arm 146 is coupled to the wall 606 via a fastener 608 and the first bolt 626 is removed, the arm 146 and the wall 606 can pivot around the second bolt 628. Pivoting around the second bolt 628 allows an operator to move the arm 146 and the camera 140 out of the way so that an interior of the first climate controlled enclosure 102 can be accessed via the door 206 of FIG. 2. After the door 206 is closed, the arm 146 and the camera 140 can be rotated back into position. Pivoting the arm 146 in this manner allows the camera 140 to be moved out of the way and returned to position in a manner that substantially retains alignment of the camera 140 with the mirror 132 and the test specimen 126.

In the example illustrated in FIG. 6, the shock isolation system 148 includes the fastener 608, a bias member 612, and multiple rounded contact points (such as balls 616). When assembled, the fastener 608 extends through an opening 632 in the arm 146 and through an opening 610 in the wall 606. The fastener 608 is secured in position (e.g., by a nut or internal threads of the opening 610). The fastener 608 is tightened sufficiently to compress or partially compress the bias member 612. In the example illustrated in FIG. 6, the bias member 612 is a conical washer (e.g., a Belleville washer); however, in other implementations a spring or another biasing member may be used.

When assembled, the balls 616 rest in recesses 614 of the wall 606 and corresponding recesses 634 of the arm 146. The recesses 634 of the arm 146 are illustrated in FIG. 6 with dotted lines to indicate that the recesses 634 in a surface of the arm 146 facing the wall 606, and are therefore not visible in the view shown in FIG. 6. The recesses 614, the recesses 634, or both, are conical and are sufficiently shallow that each of the balls 616 contacts both a sloped portion (rather than a flat bottom) of one of the recesses 614 of the wall 606 and contacts a sloped portion (rather than a flat bottom) of one of the recesses 614 of the arm 146.

During operation, the bolts 626 and 628 are secured and the camera 140 is aligned with the mirror 132 to capture images of the surface 128 of the test specimen 126. The fastener 608 is tightened sufficiently to retain the balls 616 in the recesses 614, 634 and to adjust a magnitude of a shock threshold associated with the shock isolation system 148.

When the mechanical tester 120 generates a shock that propagates to the bracket 150, the shock causes the bracket 150 to move suddenly. The greater the magnitude of the shock the larger the displacement of the bracket 150. Inertia of the arm 146 resists sudden acceleration (e.g., rapid displacement of the arm 146 with the bracket 150). If the shock is of sufficient magnitude, the relative motion of the bracket 150 and the arm 146 tends to compress the bias member 612. Compression of the bias member 612 may allow (or be caused by) motion of the balls 616 in the recesses 614, in the recesses 634, or both. For example, as explained above, the recesses 614, the recesses 634, or both, may be conical (e.g., have cone shaped walls). Thus, any translational movement of one of the balls 616 relative to the wall 606 or relative to the arm 146 is upward along a slope of a cone shaped wall of one of the recesses 614, 634. Therefore, when the shock jars the balls 616, the balls 616 move upward along the slope of the cone shaped walls of the recesses 614, 634, thereby moving the arm 146 away from the wall 606 and further compressing the bias member 612. After, the shock, the balls 616 are in an unstable position relative to the recesses 614, 634 (e.g., the balls 616 are not at a bottom of a slop of the cone shaped walls). Thus, a force applied by the bias member 612 tends to return each of the balls 616 to a stable static position at a bottom (or lowest attainable) of a respective one of the recesses 614, 634. This movement of the balls 616 allows the arm 146 to move back to a starting position (e.g., a position before the shock) relative to the bracket 150. Thus, the shock isolation system 148 automatically disengages (by allowing movement of the bracket 150 relative to the arm 146) responsive to a shock of a sufficient magnitude, and automatically re-engages (by fixing relative positions of the bracket 150 and the arm 146) after disengaging.

Figure 7:
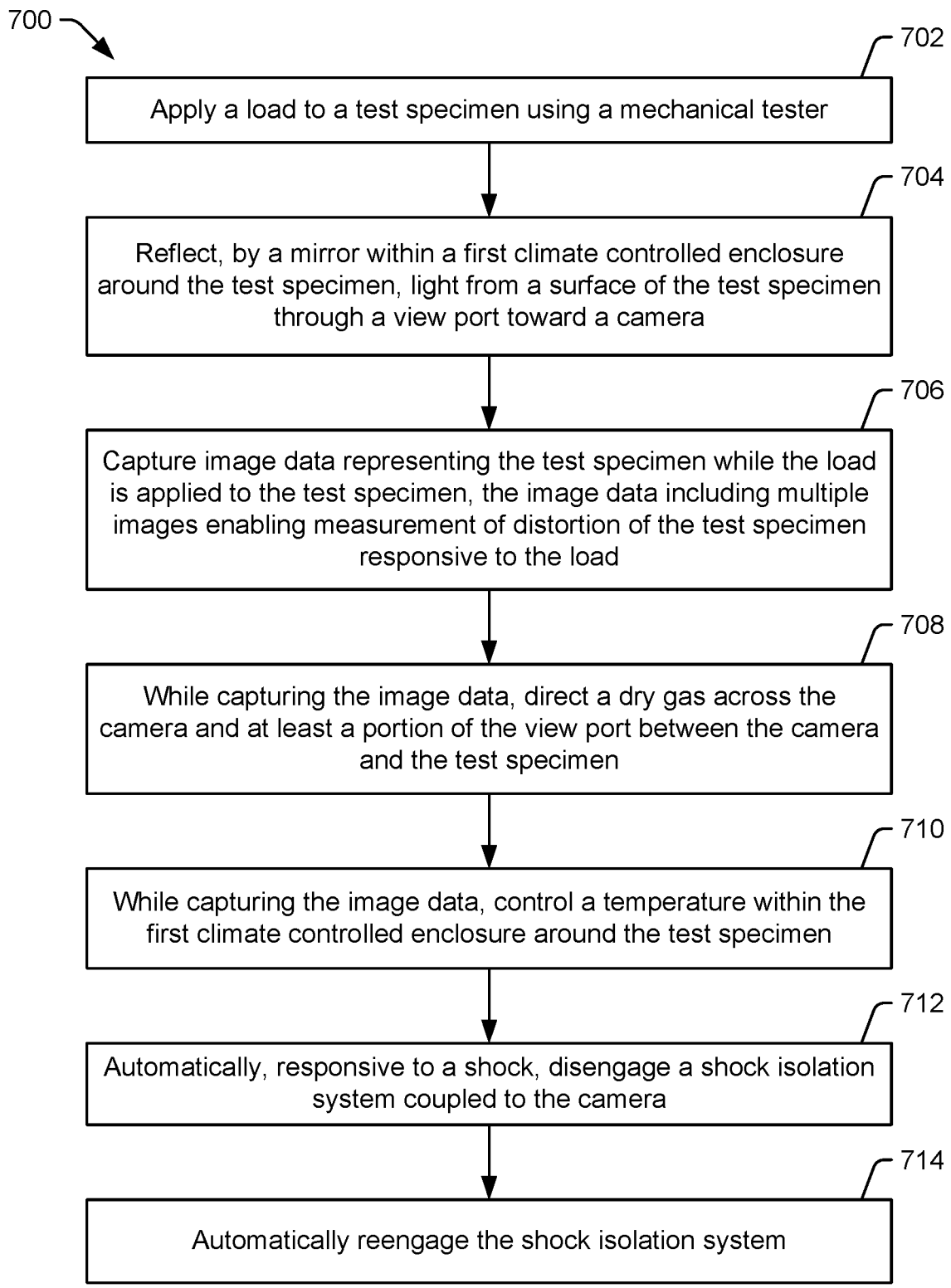
FIG. 7 is a flow chart illustrating a particular embodiment of a method of operation of the system of FIG. 1.

FIG. 7 is a flow chart illustrating a particular embodiment of a method 700 of operation of the system 100. The method 700 includes, at 702, applying a load to a test specimen using a mechanical tester. For example, the mechanical tester 120 may apply a load (such as the load 204) to the test specimen 126. The load can be a tensile load, a compressive load, or a torsional load.

In some implementations, conditions in which the test specimen 126 is subjected to the load are controlled by disposing the mechanical tester 120 and the test specimen 126 in a climate controlled enclosure, such as the first climate controlled enclosure 102. In such implementations, a surface of the test specimen 126 can be obscured by the mechanical tester 120, the first climate controlled enclosure 102, or both. In such implementations, the method 700 includes, at 704, reflecting, by a mirror within the first climate controlled enclosure, light from the surface of the test specimen through a view port of the first climate controlled enclosure toward a camera.

The method 700 also includes, at 706, using the camera to capture image data representing the test specimen while the mechanical tester applies the load to the test specimen. The image data includes multiple images enabling measurement of distortion of the test specimen responsive to the load. For example, the surface 128 of the test specimen 126 may include optically detectable features (e.g., paint dots). In this example, a first distance or relative positions of two or more of the optically detectable features can be measured (e.g., by the computing device 172) in a first image, and a second distance or relative positions of the two or more of the optically detectable features can be measured in a second image, where the second image is subsequent to the first image in a sequence of images. By comparing the first distance or relative positions and the second distance or relative positions of two or more of the optically detectable features, the distortion of the test specimen due to the load can be determined.

The method 700 also includes, at 708, while capturing the image data, directing a dry gas across the camera and at least a portion of a view port between the camera and the test specimen. In some implementations, the dry gas directed across the camera and at least the portion of a view port between the camera and the test specimen is at a different temperature than the temperature within the first climate controlled enclosure. For example, when conducting low temperature testing or high temperature testing in the first climate controlled enclosure 102, the temperature within the first climate controlled enclosure 102 may be outside a recommended operating temperature range of the camera 140. In this example, the dry gas may be warmed or cooled to keep the camera 140 within its recommended operating temperature range. Additionally, in this example, the method 700 includes, at 710, while capturing the image data, controlling the temperature within the first climate controlled enclosure. In some implementations, the temperature within the first climate controlled enclosure is controlled within a range from less than 0 degrees Celsius to greater than 100 degrees Celsius. In other implementations, the temperature within the first climate controlled enclosure is controlled within a range from less than −70 degrees Celsius to greater than 200 degrees Celsius.

In some implementations, the mechanical testing can result in a significant shock that propagates through portions of the test system. For example, if the test specimen is loaded to failure, at failure of the test specimen, the test system can experience a large shock. In such implementations, the method 700 includes, at 712, disengaging a shock isolation system coupled to the camera. For example, the shock isolation system 148 may disengaged automatically responsive to a shock resulting from failure of the test specimen. In such implementations, the method 700 also includes, at 714, automatically reengaging (e.g., returning to a reset position) the shock isolation system after the shock isolation system disengages.

Embodiments described above are illustrative and do not limit the disclosure. It is to be understood that numerous modifications and variations are possible in accordance with the principles of the present disclosure.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A system for testing mechanical properties of a test specimen, the system comprising:
   a first climate controlled enclosure;
   a mechanical tester configured to apply a load to a test specimen within the first climate controlled enclosure; and
   a second climate controlled enclosure proximate to a view port of the first climate controlled enclosure, the second climate controlled enclosure configured to enclose a camera configured to capture image data representing the test specimen, the image data including multiple images that enable measurement of distortion of the test specimen responsive to the load.

2. The system of claim 1, further comprising a mirror within the first climate controlled enclosure, the mirror positioned to reflect light from a surface of the test specimen toward the camera.

3. The system of claim 2, further comprising a housing within the first climate controlled enclosure, the housing enclosing the mirror.

4. The system of claim 1, further comprising a climate control system coupled to the first climate controlled enclosure, the climate control system configured to adjust a temperature within the first climate controlled enclosure through a range from less than 0 degrees Celsius to greater than 100 degrees Celsius.

5. The system of claim 4, wherein the range is from less than −70 degrees Celsius to greater than 200 degrees Celsius.

6. The system of claim 1, wherein the second climate controlled enclosure includes a dry gas circulation system configured to route dry gas across at least a portion of the camera and at least a portion of the view port.

7. The system of claim 1, further comprising:
   an arm;
   a camera mount coupled to the arm, the camera mount configured to retain the camera; and
   a shock isolation system configured to couple the arm to a portion of the first climate controlled enclosure and configured to automatically disengage responsive to a shock having a magnitude that satisfies a release threshold.

8. The system of claim 7, wherein the shock isolation system is configured to automatically reset and reengage after disengaging.

9. The system of claim 1, further comprising a manipulator within the first climate controlled enclosure, the manipulator configured to, while the first climate controlled enclosure is closed, retrieve the test specimen from a location within the first climate controlled enclosure and position the test specimen in the mechanical tester.

10. A system for testing mechanical properties of a test specimen, the system comprising:
    a camera mount coupled to an arm, the camera mount configured to retain a camera in a position to capture image data representing a test specimen while a mechanical tester applies a load to the test specimen, the image data including multiple images that enable measurement of distortion of the test specimen responsive to the load; and
    a shock isolation system configured to couple the arm to a portion of a test system including the mechanical tester and configured to automatically disengage responsive to a shock due to a failure of the test specimen.

11. The system of claim 10, wherein the shock isolation system is configured to automatically reset and reengage after disengaging.

12. The system of claim 10, further comprising a housing and a mirror within the housing, the mirror positioned to reflect light from a surface of the test specimen toward the camera.

13. The system of claim 10, wherein the test system includes a first climate controlled enclosure and further comprising a second climate controlled enclosure, wherein the camera mount is disposed within the second climate controlled enclosure.

14. The system of claim 13, further comprising a dry gas circulation system configured to route dry gas within the second climate controlled enclosure and across a view port between the first climate controlled enclosure and the second climate controlled enclosure.

15. The system of claim 10, wherein the shock isolation system includes:
- a fastener configured to couple the arm to the portion of the test system;
- a bias member coupled to the arm and configured to apply, to the arm, a force toward the portion of the test system; and
- multiple rounded contact points disposed between the arm and the portion of the test system, the multiple rounded contact points configured to guide the arm to a reset position after the shock isolation system disengages responsive to the shock.

16. A method of testing, the method comprising:
- capturing, using a camera, image data representing a test specimen while a mechanical tester applies a load to the test specimen, the image data including multiple images that enable measurement of distortion of the test specimen responsive to the load;
- while capturing the image data, directing a dry gas across the camera and at least a portion of a view port between the camera and the test specimen; and
- disengaging a shock isolation system coupled to the camera, the shock isolation system disengaged automatically responsive to a shock resulting from a failure of the test specimen.

17. The method of claim 16, further comprising, while capturing the image data, controlling a temperature within a first climate controlled enclosure around the test specimen, the temperature controllable within a range from less than 0 degrees Celsius to greater than 100 degrees Celsius.

18. The method of claim 17, wherein the dry gas is at a different temperature than the temperature within the first climate controlled enclosure.

19. The method of claim 17, further comprising reflecting, by a mirror within the first climate controlled enclosure, light from a surface of the test specimen through the view port toward the camera.

20. The method of claim 16, further comprising automatically reengaging the shock isolation system after the shock isolation system disengages.

* * * * *